United States Patent [19]

Andoh

[11] Patent Number: 5,345,184
[45] Date of Patent: Sep. 6, 1994

[54] HUMIDITY DETECTION CIRCUIT FOR ELECTRONIC HEAT COOKING APPARATUS

[75] Inventor: Yuuzi Andoh, Yamato-koriyama, Japan

[73] Assignee: Sharp Kabushiki Kaisha, Osaka, Japan

[21] Appl. No.: 990,241

[22] Filed: Dec. 14, 1992

[30] Foreign Application Priority Data

Dec. 16, 1991 [JP] Japan .................. 3-351714
Dec. 16, 1991 [JP] Japan .................. 3-351715

[51] Int. Cl.$^5$ ........................... G01N 27/04
[52] U.S. Cl. ........................ 324/720; 324/706; 324/721
[58] Field of Search ............ 324/105, 106, 706, 714, 324/720, 721, 71.1; 374/173

[56] References Cited

U.S. PATENT DOCUMENTS

| | | | |
|---|---|---|---|
| 3,447,075 | 5/1969 | Williams, Jr. ............... | 324/703 |
| 4,072,051 | 2/1978 | Peterson ..................... | 73/861.03 |
| 4,216,675 | 8/1980 | Nagata et al. ............... | 324/115 X |
| 4,282,480 | 8/1981 | Fujito et al. ................ | 324/676 X |
| 5,189,362 | 2/1993 | Doble ......................... | 324/106 |

FOREIGN PATENT DOCUMENTS

| | | |
|---|---|---|
| 4100318 | 7/1991 | Fed. Rep. of Germany . |
| 60-14149 | 1/1985 | Japan . |
| 60-32288 | 2/1985 | Japan . |
| 60-203811 | 10/1985 | Japan . |

Primary Examiner—Kenneth A. Wieder
Assistant Examiner—Christopher M. Tobin

[57] ABSTRACT

A humidity detection circuit includes a bridge circuit containing temperature sensing elements. The bridge circuit is connected in series to a current limiting resistance, a current controlling element and a power supply. There is a set of resistances arranged in parallel with the current limiting resistor and the bridge circuit. A voltage comparing circuit is operatively connected to the bridge circuit the current limiting resistance and the set of resistances. A control section is provided to detect the potential of a junction between the bridge circuit and the current limiting resistance. Based upon the detector potential, the humidity detection circuit changes resistance value of a resistor in the set to an optimal level so that temperature drift does not occur.

6 Claims, 7 Drawing Sheets

HUMIDITY DETECTION CIRCUIT FOR ELECTRONIC HEAT COOKING APPARATUS

BACKGROUND OF THE INVENTION (1) Field of the Invention

The present invention relates to a circuit for detecting humidity, and particularly to an improved circuit for humidity detection for detecting finishing condition of a foodstuff to be dielectrically heated in and by a heat-cooking apparatus such as, for example, an electronic range.

(2) Description of the Related Art

In prior art heat-cookers such as electronic ranges, finishing condition of a foodstuff cooked is controlled by a known means in which for example an absolute humidity detector which is used to detect vapor generated from the foodstuff with heat. The detection is placed in the vicinity of an exhaust port of a cooking chamber.

Figure 1:
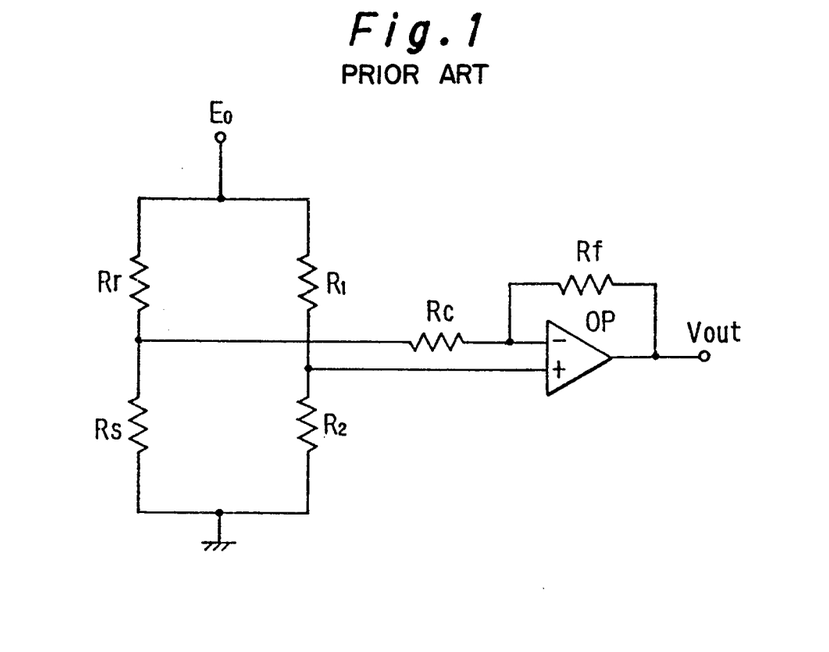
FIG. 1 is a circuit diagram showing an example of a conventional circuit for detecting humidity using platinum resistances.

FIG. 1 shows a conventional circuit for detecting humidity, wherein elements, for example, platinum resistances, having positive temperature coefficients are used as temperature sensing elements for the detector mentioned above. In the configurations of a humidity detector for detecting an absolute humidity, as shown in FIG. 1, the circuit includes two temperature sensing elements Rs and Rr. The first temperature sensing element Rs is exposed in the atmosphere, while the second temperature sensing element Rr is hermetically sealed. Both the first and second temperature sensing elements Rs and Rr are heated by themselves at approximately equal temperatures, and the first temperature sensing element Rs detects a change of heat transfer coefficient due to a temperature variation of the atmosphere by detecting a change in its own resistance value, while the second temperature sensing element Rr compensates for the temperature variation of the atmosphere. In addition, the circuit is supplied with a power supply of a source voltage Eo for activating the humidity detector, and includes two resistances, namely first and second resistances R1 and R2 which, together with the temperature sensing elements form a bridge circuit for detecting a ratio between the temperature sensing elements Rs and Rr, and a voltage converting circuit (which will be described hereinafter) for converting the ratio between the temperature sensing elements Rs and Rr into a voltage. Specifically, the aforementioned two temperature sensing elements Rs and Rr are arranged in series, one terminal of which is connected to the power supply of source voltage Eo, while other terminal is grounded. In addition, the first and second resistances R1 and R2 in series are arranged in parallel with the temperature sensing elements Rs and Rr to complete the bridge circuit. A junction between the first and second temperature sensing elements Rs and Rr, and another junction between the first and second resistances elements R1 and R2 are respectively connected to the aforementioned voltage converting circuit which in turn outputs absolute humidity amount to be detected.

Here, the junction between the two temperature sensing elements Rs and Rr is led to an inverting input terminal of an operation amplifier OP through an input resistance Rc of the OP, while the junction between the two resistances R1 and R2 is connected to a non-inverting input terminal of the operation amplifier OP. Connected to a point between the operation amplifier OP and the input resistance Rc of the OP is a negative feedback resistance Rf at its one end and the other end of which is connected to an output terminal of the operation amplifier OP. That is, the voltage converting circuit comprises OP, Rc and Rf.

The output voltage Vout outputted from the thus constructed operation amplifier OP is represented by the following formula (1):

$$Vout = -Av \times Eo \times 1/\{1 + (Rr/Rs)\} + \qquad (1)$$

$$(1 + Av) \times Eo \times 1/\{1 + (R1/R2)\}$$

where Av indicates an amplifier factor, represented by Av=Rf/Rc.

Figure 2:
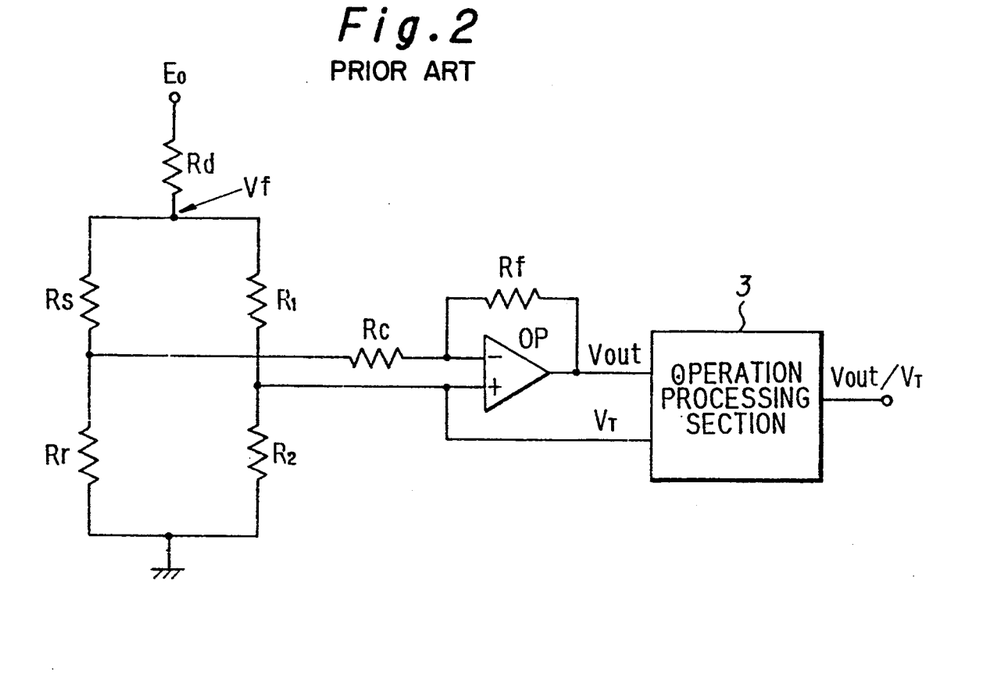
FIG. 2 is a circuit diagram showing an example of a conventional circuit for detecting humidity using thermistors.

FIG. 2 shows a conventional circuit for detecting temperature, wherein, for example, thermistors having negative temperature coefficients are used as temperature sensing elements for the detector. As shown in FIG. 2, an element having negative temperature coefficients for example such as a thermistor decreases its resistance with an elevated temperature, therefore, if the thermistor is driven by a constant voltage power supply, the self-heating temperature of the thermistor sharply rises with the atmosphere temperature elevated, and in a worst case, this results in destruction of the element. To deal with this, a current limiting resistance Rd is usually inserted into between the power supply and the subject circuit. Other configurations are largely identical with the aforesaid case in which platinum resistances are employed. That is, in the humidity detector for detecting absolute humidity, the circuit includes two temperature sensing elements Rs and Rr, the first temperature sensing element Rs is exposed in the atmosphere, whereas the second temperature sensing element Rr is hermetically sealed. Both the first and second temperature sensing elements Rs and Rr are self-heated at approximately equal temperatures, and the first temperature sensing element Rs detects a change of heat transfer coefficient due to a humidity variation of the atmosphere by detecting a change in its own resistance value, while the second temperature sensing element Rr compensates for the temperature variation of the atmosphere.

In addition, the circuit is supplied with a power supply of a source voltage Eo for activating the humidity detector, and comprises two resistances, namely first and second resistances R1 and R2 which, together with the temperature sensing elements form a bridge circuit for detecting a ratio between the temperature sensing elements Rs and Rr, a current limiting resistance Rd and a voltage converting circuit (which will be described hereinafter) for converting the ratio between the temperature sensing elements Rs and Rr into a voltage. Specifically, the aforementioned two temperature sensing elements Rs and Rr are arranged in series, one terminal of which is connected to the current limiting resistance Rd, while the other terminal is grounded. A series of the first and second resistances R1 and R2 is connected in parallel with the two temperature sensing elements Rs and Rr to complete a so bridge circuit. The other terminal of the aforementioned current limiting resistance Rd is connected to the power supply of source voltage Eo. A junction between the first and second temperature sensing elements Rs and Rr, and another junction between the first and second resistances R1 and R2 are respectively connected to the aforementioned voltage converting circuit. The output of the voltage converting circuit and a voltage $V_T$ at a point between the first and second resistances R1 and R2 are inputted to and processed by an operation processing section 3, which in turn outputs an absolute humidity to be detected.

In this voltage converting circuit, like the aforementioned case in which the platinum resistances are used, a junction between the two temperature sensing elements Rs and Rr is connected to an inverting input terminal of an operation amplifier OP through an input resistance Rc of the OP, while another junction between the two resistances R1 and R2 is connected to a non-inverting input terminal of the operation amplifier OP. Connected to an intermediate point between the operation amplifier OP and the input resistance Rc of the OP is a negative feedback resistance Rf at its one end and the other end of the resistance Rf is connected to an output terminal of the operation amplifier OP. The output voltage Vout of this voltage converting circuit, i.e., the output of the OP, and a voltage $V_T$ at an intermediate point between the two resistances R1 and R2 are processed in the operation processing section 3 in which the output Vout is divided by $V_T$ for operational correction to make Vout/$V_T$, which may be considered as absolute humidity output.

The output voltage Vout outputted from the thus constructed operation amplifier OP is represented by the following formula (2):

$$Vout = -Av \times Vf \times 1/\{1 + (Rs/Rr)\} + \qquad (2)$$

$$(1 + Av) \times Vf \times 1/\{1 + (R1/R2)\}$$

where Av indicates an amplifier factor as stated above, represented by Av=Rf/Rc, and Vf denotes a bridge circuit voltage expressed by Vf=Eo×Zs/(Zs+Rd), Zs is a combined resistance value expressed by Zs=(Rs+Rr)×(R1 +R2)/(Rs+Rr+R1+R2).

Nevertheless, in the formula (2), the value Vf varies dependent upon the resistance values of the thermistors Rs and Rr which in turn change due to variation in temperature. So, in order to compensate for this change or to correct this value, there is a method disclosed in for example, Japanese Patent Application Laid-Open No. Sho 60-32288 in which the output value Vout is divided by $V_T$, or a voltage at an intermediate point between R1 and R2. The thus defined value Vout/VT is calculated by the following formula (3), and is assumed as absolute humidity output.

$$Vout/V_T = C \times (-Av) \times 1/\{1 + (Rs/Rr)\} + \qquad (3)$$

$$C \times (1 + Av) \times 1/\{1 + (R1/R2)\}$$

where C is a coefficient.

As has been shown in formulae (1) to (3) heretofore, the ratio of the first temperature sensing element Rs to the second temperature sensing element Rr is converted into a voltage to obtain an absolute humidity.

Figure 3:
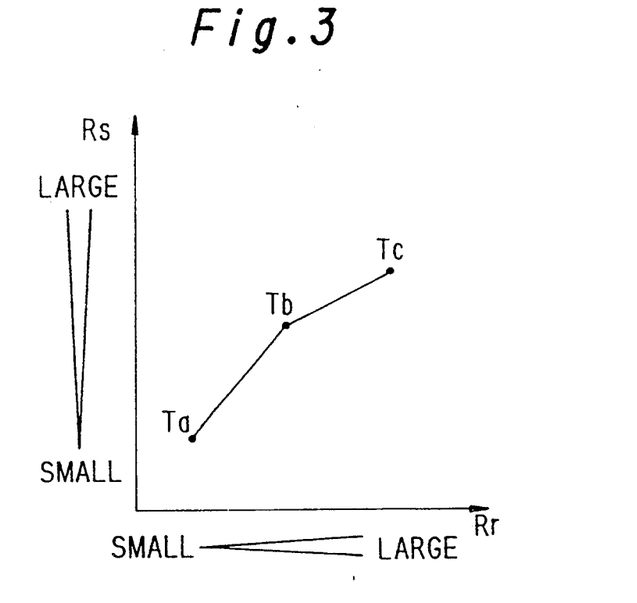
FIG. 3 is a characteristic chart showing relation between Rr and Rs of platinum resistances.
Figure 4:
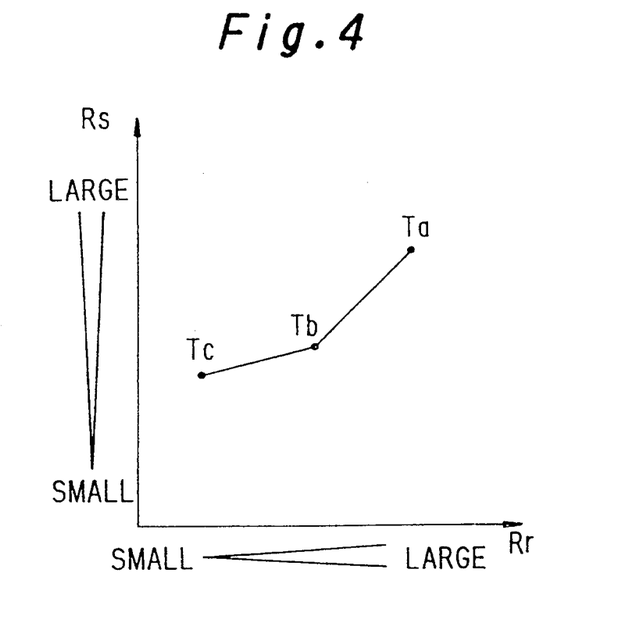
FIG. 4 is a characteristic chart showing relation between Rr and Rs of thermistors.

FIGS. 3 and 4 show Rr - Rs characteristics of the platinum resistors and the thermistors, respectively, where the atmospheric temperature is elevated from Ta through Tb to Tc, and the absolute humidity is constant between Ta and Tb, and becomes increased gradually from Tc to Tb. As is apparent from the above formula, in an ideal state, or specifically when the relation Rs=Rr holds within a temperature between Ta and Tb, the output will be constant as long as the absolute humidity is unchanged even if the humidity is changed.

However, it is extremely difficult or impossible to choose a combination of elements Rs and Rr satisfying such a relation. In practice, the relation between Rs and Rr is represented by a linear formula, that is, Rs=A×Rr+B (A, B are coefficients). In some extreme cases, even the linear relation may not hold.

For these reasons, any change in temperature with the absolute humidity unchanged sometimes cause a change in output, that is, so called temperature drift occurs.

To deal with this, the following methods (a) and (b) have been taken as measures:

(a) A resistance for correction is added to either of Rs or Rr, as disclosed in Japanese Patent Application Laid-Open No. Sho 60-14149. In this method, A in the above relation Rs=A×Rr+B is assumed to be 1 and if B is positive, then a series resistance for correction having a value corresponding to B will be connected with the element Rr. On the other hand, if B is negative, then a series resistance corresponding to B for correction is to be connected with the element Rs.

(b) As is found in Japanese Patent Application Laid-Open No. Sho 60-203811, the current flowing through the elements will be controlled in accordance with variations of resistances Rs and Rr due to changes in temperature. For example, if the temperature of the atmosphere goes down, the current is increased so as to inhibit the temperature drop, whereas, if the temperature of the atmosphere goes up, the current is decreased so as to inhibit the temperature rise. With this control, the resistance variations of Rs and Rr can be made less, and thus the temperature drift will be inhibited.

Nevertheless, the above measures (a) and (b) have drawbacks as follows, and therefore neither of these measures would work sufficiently.

That is, the measure (a) can be applied only for the case of A=1, and furthermore it is difficult to set a resistance for correction for each of practical circuits. Therefore, in the practical case, a resistance value for correction is set up such that the temperature drift falls within an allowable range determined in advance. As a result, Rs and Rr should be selected in advance to some extent.

The measure (b) might exhibit some effects of correction, but a plurality of parameters are required upon determination of circuit constants for setting up the current limit. Moreover, the apparatus needs more parts giving rise to problems in cost and design.

SUMMARY OF THE INVENTION

It is therefore an object of the present invention to provide a circuit for detecting humidity in which occurrence of the temperature drift can be inhibited readily and therefore detection of humidity precisely results without regard to the temperature of the atmosphere.

The present invention has been provided to accomplish the above object. In accordance with one aspect of the present invention, a humidity detection circuit comprises: a bridge circuit composed of a first series of at least two temperature sensing elements one of which is hermetically sealed and the other of which is exposed to the atmosphere, and a second series of at least two resistances; a power supply for activating the temperature sensing elements; a voltage converting circuit for converting a ratio of resistances to the temperature sensing elements into a voltage; a third resistance for limiting current flowing through the bridge circuit, connected serially at its one end to the bridge circuit; a voltage controlling element, disposed between the other end of the third resistance and the power supply; a resistance series of fourth and fifth resistances connected to each other, one end of the resistance series being connected to a junction between the current controlling element and the third resistance and the other end of the resistance series being grounded so as to be in parallel with the series of the third resistance and the bridge circuit, the resistance value of the fourth and fifth resistances being determined in accordance with the ratio of the third resistance to the combined resistance of the bridge circuit in operation; and a voltage comparing circuit to which a junction between the fourth and fifth resistances and another junction between the third resistance and the bridge circuit are connected separately, wherein the output of the voltage comparing circuit is inputted to the current controlling element. With this arrangement, when the resistance values of first and second temperature sensing elements changes dependent upon the variation of the atmospheric temperature based upon a reference resistance ratio of the fourth resistance to the fifth resistance preselected, the current flowing through the temperature sensing elements is regulated by the output of the voltage comparing circuit so as to keep constant the operation temperature of the temperature sensing elements, thus making it possible to prevent the occurrence of temperature drift.

In accordance with second aspect of the present invention, a humidity detection circuit comprises: a bridge circuit composed of a first series of at least two temperature sensing elements one of which is hermetically and the other which is of exposed to the atmosphere sealed, and a second series of at least two resistances; a power supply for activating the temperature elements; a voltage converting circuit for converting a ratio of resistances to the temperature sensing elements into a voltage; a third resistance for limiting current flowing through the bridge circuit, connected serially at its one end to the bridge circuit; a voltage controlling element, disposed between the other end of the third resistance and the power supply; a resistance series of fourth and fifth resistances connected to each other, one end of the resistance series being connected to a junction between the current controlling element and the third resistance and the other end of the resistance series being grounded so as to be in parallel with the series of the third resistance and the bridge circuit, the resistance value of the fourth and fifth resistances being determined in accordance with the ratio of the third resistance to the combined resistance of the bridge circuit in operation; and a voltage comparing circuit to which a junction between the fourth and fifth resistances and another junction between the third resistance and the bridge circuit are connected separately; and a variable resistance composed of a plurality of resistances each being grounded through a respective switch provided therefor; and a control section for controlling the switches, being connected to the same junction between the third resistance and the bridge circuit, with that of the voltage comparing circuit, wherein the output of the voltage comparing circuit being inputted to the current controlling element. With this arrangement, based upon a potential of the junction between the third resistance and the bridge circuit, the voltage drop of the fourth or fifth resistances as voltage dropping means is adjusted or controlled within a certain range, so that the dispersion or discrepancy in characteristics between the two temperature sensing elements is compensated for, and consequently the detection accuracy can be improved. It should be noted that the temperature sensing elements used in the present invention may have either positive or negative temperature characteristics.

DESCRIPTION OF THE PREFERRED EMBODIMENTS

The present invention will be described with reference to the accompanying drawings.

Figure 5:
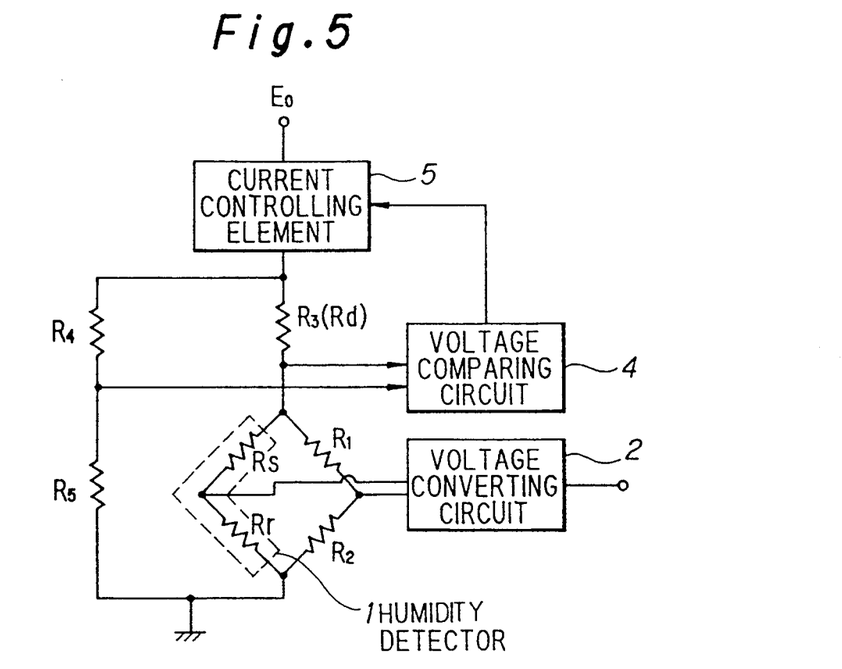
FIG. 5 is a block diagram showing a circuit for detecting humidity according to a first embodiment of the present invention.

First, FIG. 5 is a schematic block diagram of a circuit for detecting humidity according to one embodiment of the present invention. In this figure, a humidity detector 1, having the same structure described in the above prior art, is composed of a bridge circuit comprising first and second temperature sensing elements Rs and Rr (a first resistance series) connected in series and first (R1) and second (R2) resistances connected in series (a second resistance series). A junction between the first and second temperature sensing elements Rs and Rr and another junction between the first and second resistances are led to a voltage converting circuit 2, respectively (R1 and R2) in the same manner as described in the prior art shown in FIG. 1.

Meanwhile, the circuit of the present invention includes a third resistance (a current limiting resistance) R3 (or Rd) connected serially at one end with the bridge circuit for limiting current flowing into the bridge circuit. The third resistance R3 is connected at its other end to a current controlling element 5, which in turn is connected to a power supply having a source voltage of Eo. In addition, fourth and fifth resistances R4 and R5 are provided in series forming a third resistance series. Here the resistance values of R4 and R5 are determined under consideration of the ratio of the resistance values of the resistance R3 to that of the combined resistance of the bridge circuit in operation.

The combined series of the fourth and fifth resistances R4 and R5 is connected at the R4's end to a junction between the third resistance R3 and the current controlling element 5 and is arranged in parallel with the series of the third resistance R3 and the bridge circuit. A junction between the fourth and fifth resistances R4 and R5 and another junction between the third resistance R3 and the bridge circuit are individually connected to a voltage comparing circuit 4, which output in turn is inputted to the current controlling element 5.

Here, the detection of absolute humidity is carried out in the same manner described above by the bridge circuit comprising the temperature sensing elements, while the values of the fourth and fifth resistances R4 and R5 are determined by the combined resistance value Zs of the bridge circuit, which was referred to heretofore and is calculated from the resistances of the temperature sensing elements in operation, and the current limiting resistance value Rd (or the third resistance value R3). That is, $$R4/R5 = Rd/Zs$$

The humidity detection circuit of the present invention basically has the structure described above, and next description will be made of a case in which the temperature sensing elements Rs and Rr employ elements having negative temperature co-efficients, such as, for example, thermistors.

Figure 6:
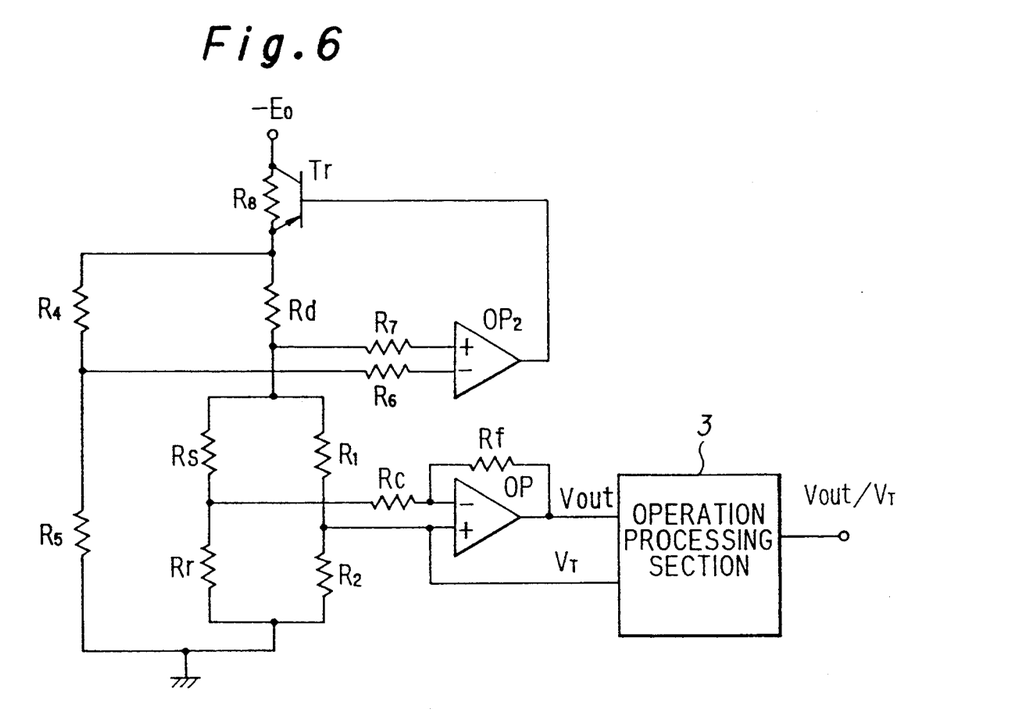
FIG. 6 is a schematic block diagram showing one feature of the circuit shown in FIG. 5.

FIG. 6 shows an embodiment in which thermistors are used as the temperature sensing elements Rs and Rr. Here a voltage converting circuit 2 containing a bridge circuit and an operation processing section 3 has the same structure as in the prior art shown in FIG. 2. In this embodiment, a junction between fourth and fifth resistances R4 and R5 is connected through a resistance R6 to an inverting input terminal of an operation amplifier OP2, whereas a junction between a current limiting resistance Rd or a third resistance R3 and the bridge circuit is led to a non-inverting input terminal of the operation amplifier OP2 through a resistance R7. On the other hand, a junction between the fourth resistance R4 and the current limiting resistance Rd is led to the emitter of a transistor Tr. Arranged in parallel between the emitter and the collector of the transistor Tr is a current bias resistance R8, and the collector is connected to a power supply having a negative source voltage of Eo. An output terminal of the operation amplifier OP2 is connected to the base of the transistor Tr. In this arrangement, the resistances R6, R7 and the operation amplifier OP2 constitute the voltage comparing circuit 4 shown in FIG. 5, while the transistor Tr and the current bias resistance form the current controlling element 5 shown in FIG. 5.

Now description will be made of operations of one embodiment of the present invention in which the circuit arrangement is constructed as shown in FIGS. 5 and 6, or there are provided the fourth and fifth resistances R4 and R5 are provided as well as the voltage comparing circuit 4 and the current controlling element 5. First, if the atmosphere temperature exceeds a preselected temperature (at which the operational resistances Rs and Rr of the thermistors are determined), the voltage difference between the both terminals of the bridge becomes small (or the potential becomes close to the ground side). Accordingly the output of the operation amplifier OP2 of the voltage comparing circuit 4 becomes small (or become close to the around side), this causes the current flowing between through the collector and emitter of the transistor Tr in the current controlling element 5 to become small. In accordance with the decrease of the current just mentioned, current through the thermistors Rs and Rr decreases so as to cause the self-heating temperature of the thermistors Rs and Rr to fall. Accordingly, the combined resistance Zs of the bridge will be stabilized in correspondence with the current limiting resistance Rd on the basis of the ratio between the fourth and fifth resistances R4 and R5. As a result, even if the atmosphere temperature goes up, the self-heating temperature of the thermistors Rs and Rr are unchanged at the preselected temperature. This means no occurrence of temperature drift.

Next, description will be made of means for conducting humidity detection using an apparatus of the present invention.

Figure 7:
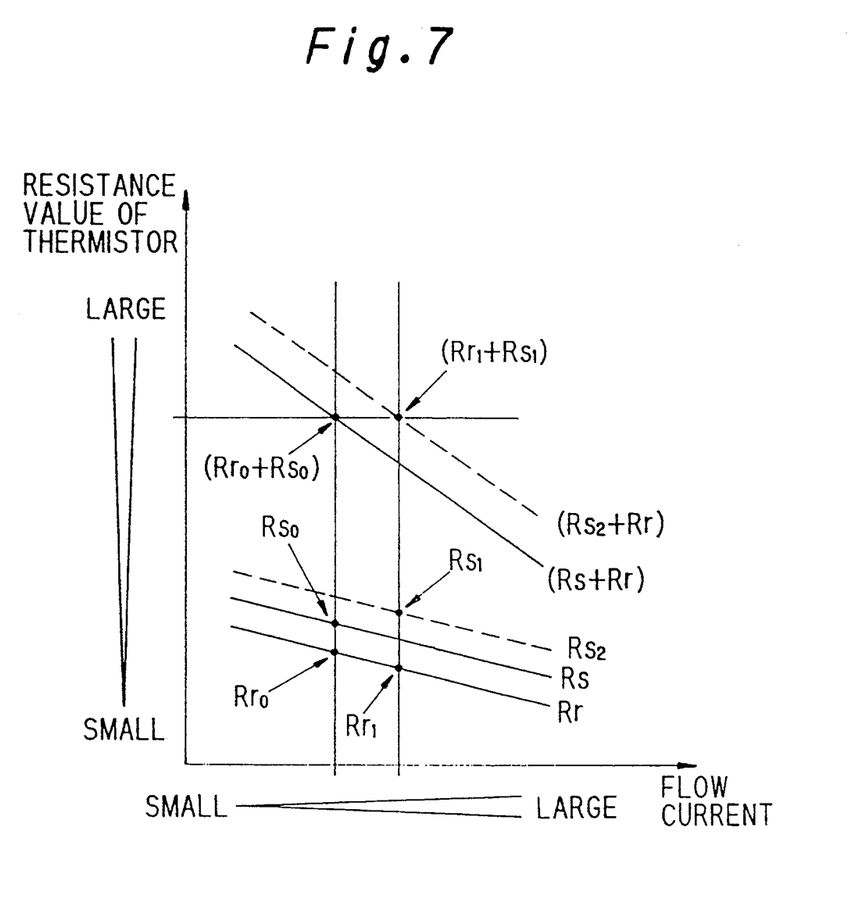
FIG. 7 is a chart for illustrating the operations of the circuit shown in FIG. 6.

FIG. 7 shows characteristics of dependence of the thermistor resistances Rs, Rr and Rs+Rr upon the flow current when the humidity is changed. In the figure, a line $Rs_2$ indicates the resistance when the humidity is increased. In the circuit of the present invention, the value Rs+Rr can be kept constant regardless of variations of the atmospheric temperature. For this reason, when the resistance value Rs+Rr changes into $Rs_2$+Rr in response with increase in humidity, the current increases such that a relation (Rs+Rr)=($Rs_2$+Rr) holds. At this time, the resistance values of the thermistors change from $Rs_0$ and $Rr_0$ to $Rs_1$ and $Rr_1$, respectively. As a result, the value Rs/Rr changes making it possible to effect humidity detection as used to be conducted.

Although the description has been made on a case in which thermistors of temperature sensing elements having negative temperature co-efficients are used, it is apparent that use of temperature sensing elements, such as of platinum, having positive temperature characteristics, can be handled by commuting the input terminals of the operation amplifier OP for one another.

According to the apparatus of the embodiment described above, occurrence of the temperature drift can be prevented by an uncomplicated means so that it is possible to detect humidity precisely regardless of the condition of the atmospheric temperature.

Figure 8:
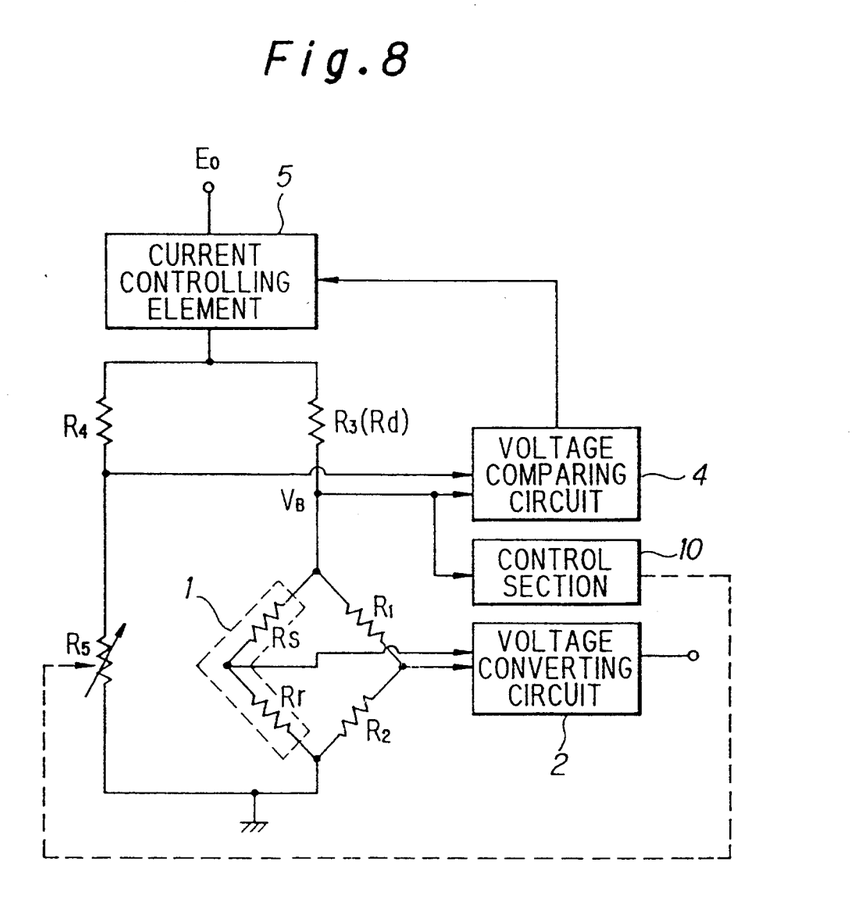
FIG. 8 is a block diagram of a circuit for detecting humidity according to a second embodiment of the present invention.

Next, a second embodiment of the present invention will be described based upon the accompanying drawings. FIG. 8 is a schematic block diagram showing a circuit for detecting humidity according to a second embodiment of the present invention.

This circuit is largely similar to the first embodiment shown in FIG. 5 except that a controlling section 10 is provided and the resistance R5 is variable in accordance with the output of the controlling section. Accordingly, the corresponding members are allotted with the same reference numerals as those shown in FIGS. 5 and 6.

As is shown in FIG. 8, a bridge circuit composed of a temperature sensing elements Rs and Rr, and resistances R1 and R2. This bridge is adapted to extract a humidity change as an imbalanced voltage, the thus obtained imbalanced voltage is inputted into a voltage converting circuit. The input voltage is amplified to an appropriate voltage level to be outputted. The output changes dependent upon variations in humidity. Any one of the above temperature sensing elements is set exposed in the atmosphere in which humidity should be detected, whereas the other one is hermetically seated from the atmosphere so as to detect only the temperature of the atmosphere. The bridge circuit is serially connected to a resistor R3 (Rd) as a third resistance. In addition, a series of resistors R4 and R5 as fourth and fifth resistance is arranged in parallel with the series of the bridge circuit and the resistor R3.

Figure 9:
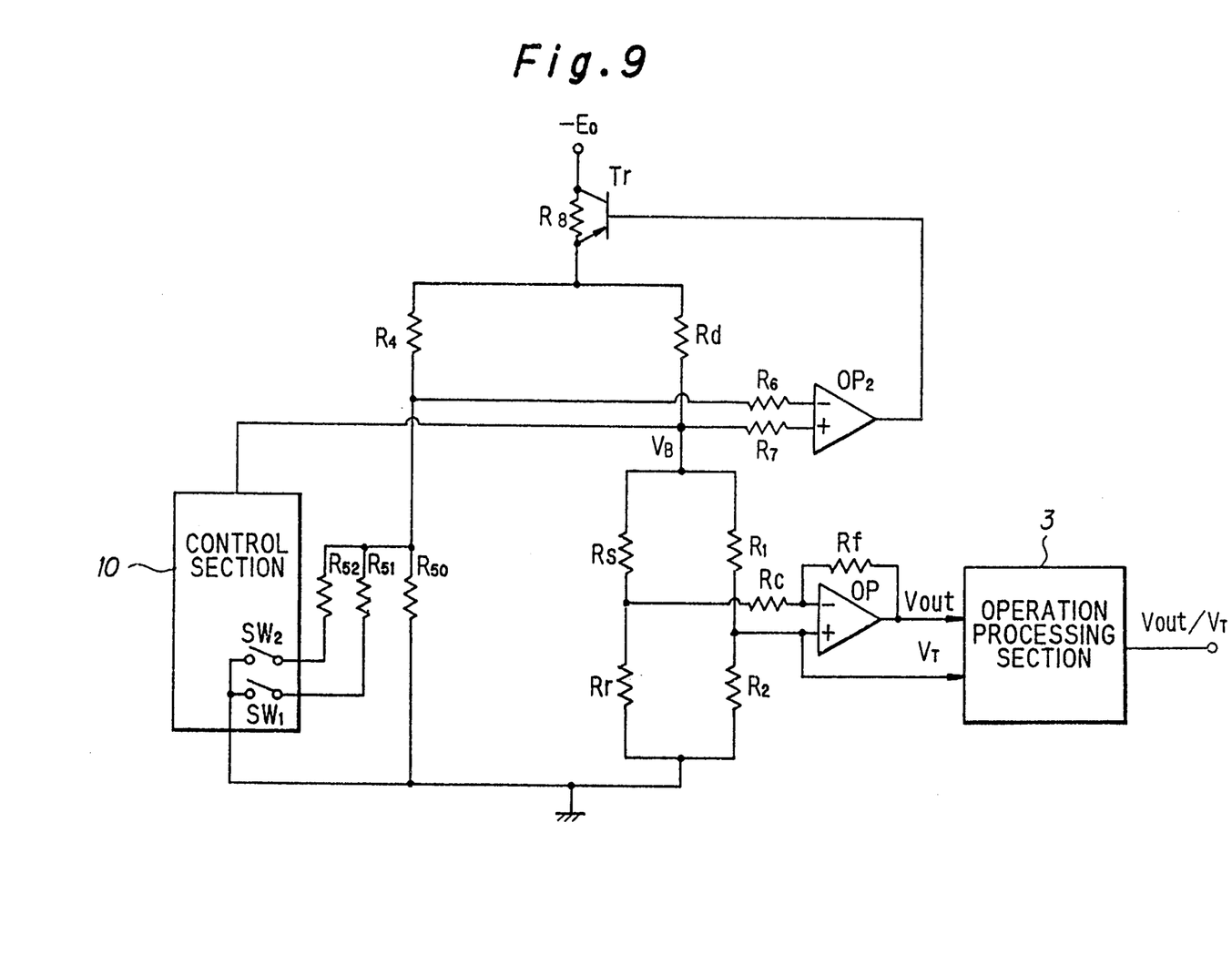
FIG. 9 is a schematic block diagram showing one feature of the circuit shown in FIG. 8.

This resistor R5 is conceptionally variable, and more specifically, comprises a plurality of fixed resistors connectable in parallel to the resistor R50, as shown in FIG. 9.

The feature shown in FIG. 9 is basically similar to that in FIG. 6 of the first embodiment in which the temperature sensing elements Rs and Rr have negative temperature characteristics, but is adapted to change the effective resistance value of the resistor R50 by selecting resistances R51 and R52 to be connected to the resistor R50 by means of switches. A junction between the resistors R4 and R50, and another junction between the resistor R3 and the bridge circuit are connected separately to a voltage comparing circuit 4, so that the potentials are compared between both the junctions by an operation amplifier OP2 shown in FIG. 9. Based on the compared result, operations of a current controlling element 5 is controlled. A potential VB at a junction between the resistor R3 and the bridge circuit is inputted to a control section 10. The control section 10 controls the switches or turns on and off the switches in accordance with the potential VB, so that the resistors are selected to be connected in parallel with the resistor R50. In other word, by this operation of the control section 10, the operation temperature of the temperature sensing elements is controlled to be nearly constant without regarding to the magnitude of the initial resistance value.

The humidity detection circuit thus arranged of the second embodiment of the present invention operates in the following manner so as to compensate for temperature drift and conducting humidity detection.

Figure 10:
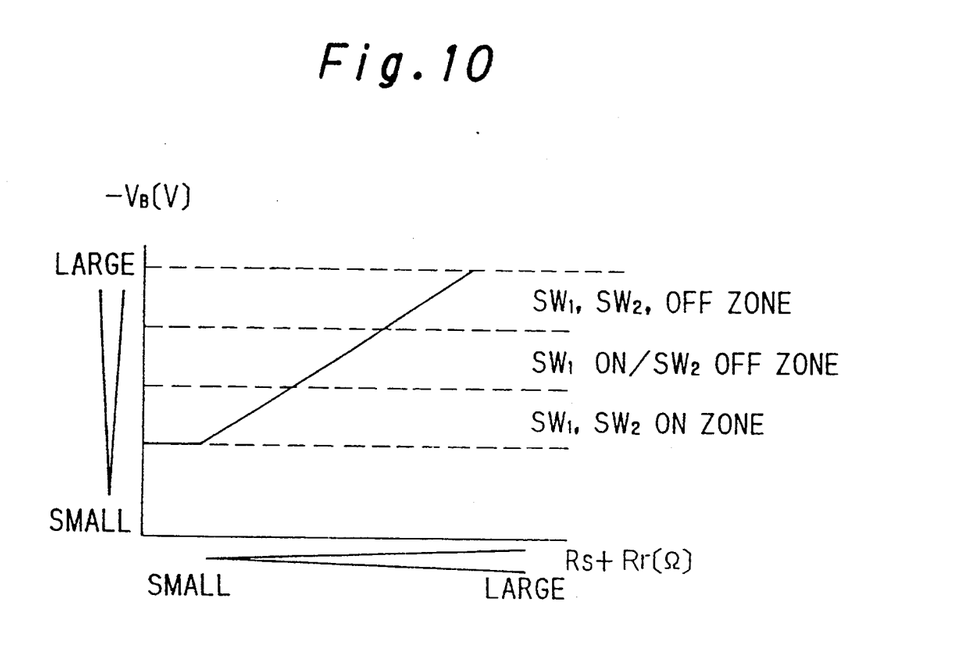
FIG. 10 is a chart for illustrating the operations of the circuit shown in FIG. 9.
Figure 11:
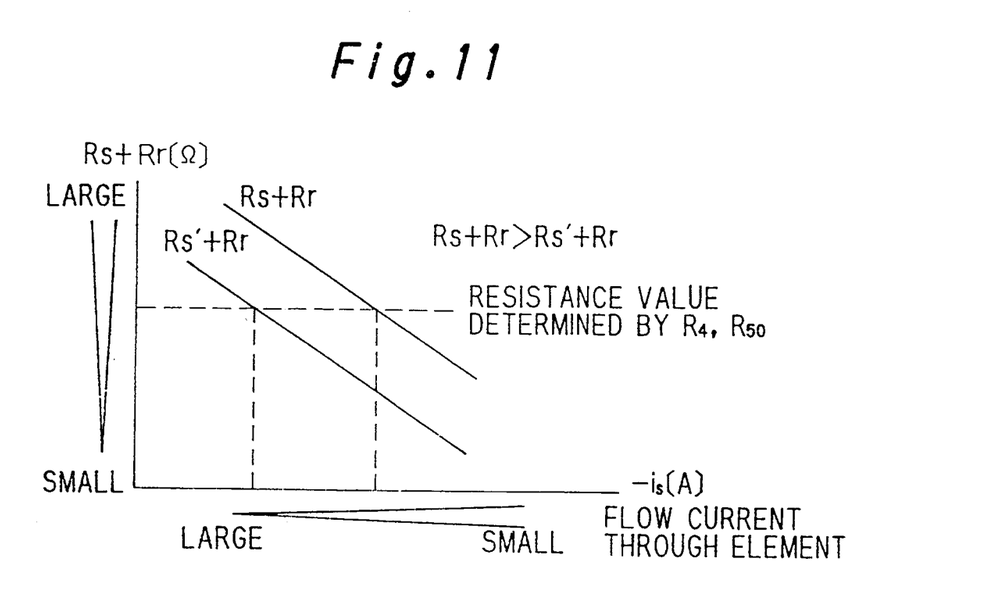
FIG. 11 is a chart for illustrating the operations of the circuit shown in FIG. 9.

First, before measurement of humidity, switches SW1 and SW2 incorporated in the control section 10 are kept off. Therefore, the resistor R4 is connected serially only with the resistor R50. That is, the combined resistance Rs+Rr of the temperature sensing elements Rs and Rr is determined in accordance with the ratio between the resistance R4 and R50. At this time, the voltage VB applied between both end terminals of the bridge circuit varies as shown in FIG. 10 dependent on the magnitude of the initial value of the combined resistance Rs+Rr. This is because that if the initial resistance value is large as shown in FIG. 11, the temperature sensing elements is required to be flowed with a large amount of current (large in negative direction) so as to change the resistance value into a certain constant level.

Accordingly, the value VB obtained on a condition of a preset atmospheric temperature represents an initial value of Rs+Rr. If the Rs+Rr determined by the R4 and R50 is adjusted near the upper boundary of a range in which the Rs +Rr is to be used, the switches SW1 and SW2 are selectively turned on and off in accordance with the value VB. As a result, the combined value of the resistance of resistors 50, R51 and R52 is changed so that the operation temperature of the temperature sensing elements is controlled to be nearly constant without regarding to the magnitude of the initial resistance value. Here, the operation points of the SW1 and SW2 are determined in advance in the control section 10, and three operational states are set up as shown in FIG. 10.

Although two resistor R51 and R52 are exemplified as resistances for drift compensation in this embodiment, this should not limit the invention, and three or four resistances may be employed. In such cases, the drift the operation temperature of the temperature sensing elements can be controlled to be constant, and accordingly, fluctuation in the output of the humidity sensor can be decreased, although the switches are required as many as the given resistances.

Thus, once switches are selectively set up by the control section 10, the state will be maintained. For instance, this setup is effected upon manufacturing, the state will be maintained from then on. In accordance with the thus setup Rs+Rr, the temperature sensing elements are controlled to be constant in temperature upon detection of humidity. That is, detection of humidity can be effected with the temperature drift prevented.

As discussed above, according to the present invention, the easily performed adjustment and control in a production line or other field, can prevent the temperature drift due to the disagreement in characteristics between two temperature sensing elements, so that the detection accuracy can be improved as well as the production yield. In accordance with this embodiment, the temperature drift is compensated by changing the resistance level, but in order to change the applied voltage to the resistance R50 it is also possible to apply an inverse bias to the resistance R50 from the outside of the circuit.

As is apparent from the foregoing description, according to the present invention, a difference between the first and second temperature elements is compensated for by means for adjusting potential drop, so that the detection accuracy of humidity detection circuit can be improved.

What is claimed is:

1. A humidity detection circuit comprising:
    a bridge circuit composed of a first resistance series of at least two temperature sensing elements connected in series, one of which is hermetically sealed and the other of which is exposed to the atmosphere, and a second resistance series of at least two resistances;
    a power supply operatively connected to said temperature sensing elements for activating said temperature sensing elements;
    a voltage converting circuit for converting a ratio of the resistance of said temperature sensing elements into a voltage;
    a current limiting resistance, having two ends, for limiting current flowing through said bridge circuit, connected in series at one end to said bridge circuit;
    a current controlling element, disposed between the second end of said current limiting resistance and said power supply;
    a third resistance series formed of a plurality of resistances connected to each other, one end of said third resistance series being connected to a junction between said current controlling element and said current limiting resistance and the other end of said third resistance series being grounded so as to be in parallel with current limiting resistance and said bridge circuit, the resistance value of said plurality of resistances being determined in accordance with the ratio of said current limiting resistance to the combined resistance of said bridge circuit in operation; and
    a voltage comparing circuit having a first connection between said plurality of resistances and a second connection between said current limiting resistance and said bridge circuit each of said connections being separate;

wherein the output of said voltage comparing circuit is inputted to said current controlling element.

2. A humidity detection circuit comprising:

a bridge circuit composed of a first resistance series of at least two temperature sensing elements connected in series, one of which is of hermetically sealed and the other of which is exposed to the atmosphere, and a second resistance series of at least two resistances;

a power supply operatively connected to said temperature sensing elements for activating said temperature sensing elements;

a voltage converting circuit for converting a ratio of the resistances of said temperature sensing element into a voltage;

a current limiting resistance having two ends for limiting current flowing through said bridge circuit, connected in series at one end to said bridge circuit;

a current controlling element disposed between a second end of said current limiting resistance and said power supply;

a third resistance series formed of a plurality of resistances connected to each other, one end of said third resistance series being connected to a junction between said current controlling element and said current limiting resistance and the other end of said third resistance series being grounded so as to be in parallel with the series of said current limiting resistance and said bridge circuit, the resistance value of said resistances of said third resistance series being determined in accordance with the ratio of said current limiting resistance to the combined resistance of said bridge circuit in operation; and a voltage comparing circuit having a first connection between said plurality of resistances of said third resistance series, a second connection between said current limiting resistance and said bridge circuit each of said connections being separate, an output of said voltage comparing circuit being inputted to said current controlling element;

said third resistance series including a variable resistance composed of a plurality of resistances each being grounded through a respective switch provided therefor; and a control section for controlling said switches, being connected to the second connection between said current controlling resistance and said bridge circuit, 3. A humidity detection circuit according to claim 1, wherein said temperature sensing elements have positive temperature coefficients.

4. A humidity detection circuit according to claim 1, wherein said temperature sensing elements have negative temperature coefficients.

5. A humidity detection circuit according to claim 2, wherein said temperature sensing elements have positive temperature coefficients.

6. A humidity detection circuit according to claim 2, wherein said temperature sensing elements have negative temperature coefficients.

* * * * *